(12) United States Patent
Ahn et al.

(10) Patent No.: US 6,995,297 B1
(45) Date of Patent: Feb. 7, 2006

(54) HERB MEDICINE COMPOSITION TO BE CONTAINED IN SANITARY MATERIALS FOR INFANTS

(76) Inventors: Deuk Hun Ahn, 101-402, Songrim Apt. 2434, Namsan-3-dong, Joong-ku, Taeku 700-443 (KR); In Jin Baek, 101-402, Songrim Apt. 2434, Namsan-3-dong, Joong-ku, Taeku 700-443 (KR); Seoung Hwan Park, 301-1410 GosanNobyun Town, 498 Siji-dong, Soosung-ku, Taeku 706-220 (KR); Dong Hun Seo, 112-205 Manchon-1-cha-Woobang Apt., Manchon-3-dong, Soosung-ku, Taeku 706-023 (KR); Jung Hwan Baek, 104-313 Whasungssangyongn Town, Soosung-4-ga, Soosung-ku, Taeku 706-034 (KR)

( * ) Notice: Subject to any disclaimer, the term of this patent is extended or adjusted under 35 U.S.C. 154(b) by 251 days.

(21) Appl. No.: 10/030,737

(22) PCT Filed: Jul. 12, 2000

(86) PCT No.: PCT/KR00/00752

§ 371 (c)(1),
(2), (4) Date: May 24, 2002

(87) PCT Pub. No.: WO01/03749

PCT Pub. Date: Jan. 18, 2001

(30) Foreign Application Priority Data

Jul. 13, 1999 (KR) .................... 1999-28249

(51) Int. Cl.
*A61F 13/50* (2006.01)
*A61F 13/20* (2006.01)

(52) U.S. Cl. ..................... 604/360; 604/367
(58) Field of Classification Search ............... 604/367, 604/358–360, 378
See application file for complete search history.

(56) References Cited

U.S. PATENT DOCUMENTS 5,466,452 A * 11/1995 Whittle .................. 424/750
5,753,242 A * 5/1998 Nakamura et al. ......... 424/401
6,027,728 A * 2/2000 Yuen ..................... 424/728
6,338,855 B1 * 1/2002 Albacarys et al. ........ 424/409

FOREIGN PATENT DOCUMENTS

CN 1072599 * 6/1993
CN 1099827 * 3/1995
CN 1178705 * 4/1998

* cited by examiner

*Primary Examiner*—Michele Kidwell
(74) *Attorney, Agent, or Firm*—Mayer, Brown, Rowe & Maw LLP

(57) ABSTRACT

The present invention relates to her medecine composition to be contained in sanitary materials for infants, which comprises Sophorae flavescens. Preferably, the composition of the present invention further contains one or more components selected from a group consisting of Phellodendri Cortex, *Artemisia* Folia, *Dictamnus* alpus and alum, besides Sophorae flavescens.

3 Claims, 2 Drawing Sheets

HERB MEDICINE COMPOSITION TO BE CONTAINED IN SANITARY MATERIALS FOR INFANTS

TECHNICAL FIELD

The present invention relates to an herb medicine composition to be contained in sanitary materials, which contains herb medicine extracts to prevent diaper rash and to relieve various skin diseases due to feces and urine in infants. In particular, the composition of the present invention can be applied to diaper and wet tissue among sanitary materials for infants.

BACKGROUND ART

Most diaper rash occurs due to buttocks region contaminated by feces and urine. Diaper rah occurs around annus because of ammonia released from urine by the action of urea degradation bacteria from feces or because of irritation by feces, and it is characterized by rubefaction, blister and superficial ulcer. In particular, in case of female infants, since they are weak in immunity compared to adults, and moreover, vulva is structurally closer to annus, it is likely to result in vulvar infection.

In case of paper diaper used widely currently, exterior vinyl cover does not allow leakage of moisture, and this is the same as window-blocked bathroom, thereby leading to fungal and bacterial multiplication. In particular, infants have to use diaper for a certain amount of period, and due to weak skin, despite of parents' continuous observation, rash should be repeated. Thus, whenever rash occurs, inconvenience of applying cream, ointment and spread of powder cannot be avoided.

Further, even in case of wet tissue for infants that have been widely used up to the present, as its main component is water, there has no special action other than cleaning.

The inventors of the present invention have conducted studies to prepare sanitary materials which have cleaning function while relieving itch due to various skin diseases and also diaper rash due to waste of infants. As the result, the inventors discovered that when herb medicine extract is spread on skin-contacting pad of diaper or is formulated into wet tissue, the herb medicine contained brings an effect of relieving skin irritation at the time of urination and bowel movement while cleaning the skin, and based on this, completed the present invention.

The object of the present invention is to provide a composition for sanitary materials, which protects skin of infants at the time of evacuation, by using herb medicine component effective for prevention and treatment of diaper rash.

DISCLOSURE OF THE INVENTION

The present invention relates to an herb medicine composition for infant sanitary materials, which contains Sophorae flavescens.

Specifically, the present invention is directed to an herb medicine composition to be applied to sanitary materials to prevent and treat diaper rash and sore, and relates to an herb medicine composition to be contained in sanitary materials, which contains Sophorae flavescens as main component having effects of removing dampness and itch as well as having antibiotic and antiphlogistic activity.

Although the composition of the present invention can sufficiently accomplish its object by using Sophorae flavescens alone, it is more preferable to further contain one or more herb medicine selected from a group consisting of Phellodendri Cortex, *Artemisia* Folia, *Dictamnus* alpus and alum, and the content of each component based on total dried weight of herb medicine composition is 20–98% by weight of Sophorae flavescens, 2–50% by weight for Phellodendri Cortex, 2–30% by weight for *Artemisia* Folia, 1–35% by weight for *Dictamnus* alpus, and 10–40% by weight for alum. It is more preferable to contain Sophorae flavescens, Phellodendri Cortex, *Artemisia* Folia, *Dictamnus* alpus and alum are all. Particularly preferred content based on total dried weight of the composition is 25–45% by weight, 10–25% by weight, 5–20% by weight, 3–10% by weight and 15–30% by weight, respectively.

The composition ratio of herb medicine enumerated above was obtained based on clinical test and animal test on herb medicine which is useful for infants diaper rash. If the ratios are higher than upper limit or lower than lower limit, it causes a problem of decrease in appearance of pad and its absorbency, in case of diaper, as well as the efficacy required in the present invention.

According to the description in the Korean Pharmacopoeia and the conventional oriental medicine references, Sophorae flavescens is mainly used for external use due to its bitter taste, and used clinically as cataplasm or detergent in treatment of skin disease with serious itch and eczema, skin pyosis and vulvar pruritis due to anti-trichomonas activity.

Phellodendri Cortex exhibits germicidal activity against *E. coli*, typhus and cholera bacilli, and also has antibiotic activity against Gram-positive, Gram-negative and gonococcus. Berberin among the ingredients of Phellodendri Cortex has a strong local astringency and thus it is externally used for pruritic skin diseases, removing heat toxicity of wound region.

*Artemisia* Folia is used in the treatment of women's diseases such as menstrual irregularity and hysterorrhea, and active against gonococcus etc. and externally used in treating eczema and skin pruritis.

*Dictamnus* alpus has effect of eliminating heat, poisoning and dampness, thus used in treatment of skin eczema, pruritis via wound cleaning and powder spread.

Alum has a strong astringent activity and an effect of removing dampness and itch, thus gives freshness to infected region by removing discomfort and bad smell, thus mainly used for external use as an astringent for skin mucous membrane infection or as gargles for the purpose of local astringency.

Herb medicines enumerated above, that is, Galla Rhois, Sophorae flavescens, Phellodendri Cortex, *Artemisia* Folia, *Dictamnus* alpus and alum all exhibit antibiotic and anti-itch effect while being harmless to human, thus are clinically used frequently. In particular, they contain strong astringent ingredient that rapidly dries local infection region, and when spread to rash, they give freshness due to their unique cold property; further their drying effect allows infant skin to be kept dry. Therefore, when infants having rash uses sanitary material of the present invention, particularly, diaper, evaporation of drug substance with urine causes evaporation of heat from the skin, leading to cooling of local rash region, and contraction of blood vessel results in decline of inflammation and cool freshness at the rash region.

For a composition to be contained in sanitary materials, Sophorae flavescens, Phellodendri Cortex, *Artemisia* Folia, *Dictamnus* alpus and alum can be formulated, respectively, into a type selected from powder, extracts and infusion. For example, effective component of said herb medicines can be extracted with water and can be used by mixing with alum extracts.

The composition of the present invention can be formulated into powders, solutions, suspensions or gels with a pharmaceutically accepted carrier depending on physicochemical properties of the active substance. Further, the composition of the present invention can contain other additives. Liquid formulation is particularly preferred for the composition of the present invention in view of the utility, but if necessary, other formulation such as powders, spray, gels etc. can be applied.

Herb medicine composition of the present invention can be applied to diaper and wet tissue among sanitary material for infants.

In case of diaper adopting said composition, the composition can be applied to whole absorbent matrix or diaper surface only. In case of applying to whole absorbent matrix, there is a disadvantage that absorbency of matrix itself is decreased, thus it is more preferable to spread the composition of the present invention only on the surface where excrement should pass when absorbed into matrix. As a single example, primary pad made of cotton cloth or paper sheet on which the composition of the present invention was sufficiently spread, can be put on conventional diaper and used. In case of preparing the primary pad, for example, it is preferred to spread about 0.05–2 g, as dried weight of extracts, of composition of the present invention on a cotton cloth of 25 cm×10 cm, more preferably, 0.1–1 g.

As another method of applying the composition of the present invention, the composition can be formulated into powder and spread on overall diaper to allow active substance mixed with excrement to react on skin side without affecting the absorbency of matrix itself.

Further, the composition of the present invention can be mixed with natural pulp and prepared into matrix or surface sheet.

The composition of the present invention can be applied according to any method by which active substance melted into excrement can function at the skin, as long as it does not reduce absorbency of matrix.

In addition, diaper adopting the composition can further include absorption-stimulating supplementary pad. The absorption-stimulating supplementary pad contains Discorea Rhizoma, and it leads to faster absorption of excrement into diaper and to keep skin dry, thereby increasing the effect of the present invention. Discorea Rhizoma is obtained by drying rootstock of Dioscorea japonica, and as it contains starch, it is useful as a tonic in treatment of diarrhea and hysterorrhea.

The present invention adopts cataplasm therapy among general therapies for local rash, thereby naturally protecting infant skin at the time of evacuation by drug substance spread on diaper itself. Even though urine might contact with skin, the spread drug substance keeps the skin smooth, prevents rash, and it exhibits its efficacy upon urination. Further, until the drug is completely diluted by repeated urination, the efficacy of the pad of the present invention lasts. In case of infants suffering from rash, the diaper adopting the composition of the present invention is moistened by spray of small amount of water, and then applied to the rash, thereby allowing cataplasm. In this case, infants would feel freshness due to drug effect rather than discomfort due to wet diaper.

Additionally, the composition of the present invention is harmless to human due to use of natural drug substance, and has no negative effects despite of its long-term use. Therefore, herb medicine composition of the present invention can accomplish the intended effect by applying to whenever diaper is used.

In addition, in case of wet tissue adopting said herb medicine composition, the composition should be in a state of aqueous solution of herb medicine extracts to apply to wet tissue, and the concentration is preferably 3–25% as dried weight of extract, and more preferably 4–15%.

The herb medicine composition of the present invention can be applied in any way to protect skin from diaper rash while not reducing function of wet tissue.

EXAMPLES

Figure 1:
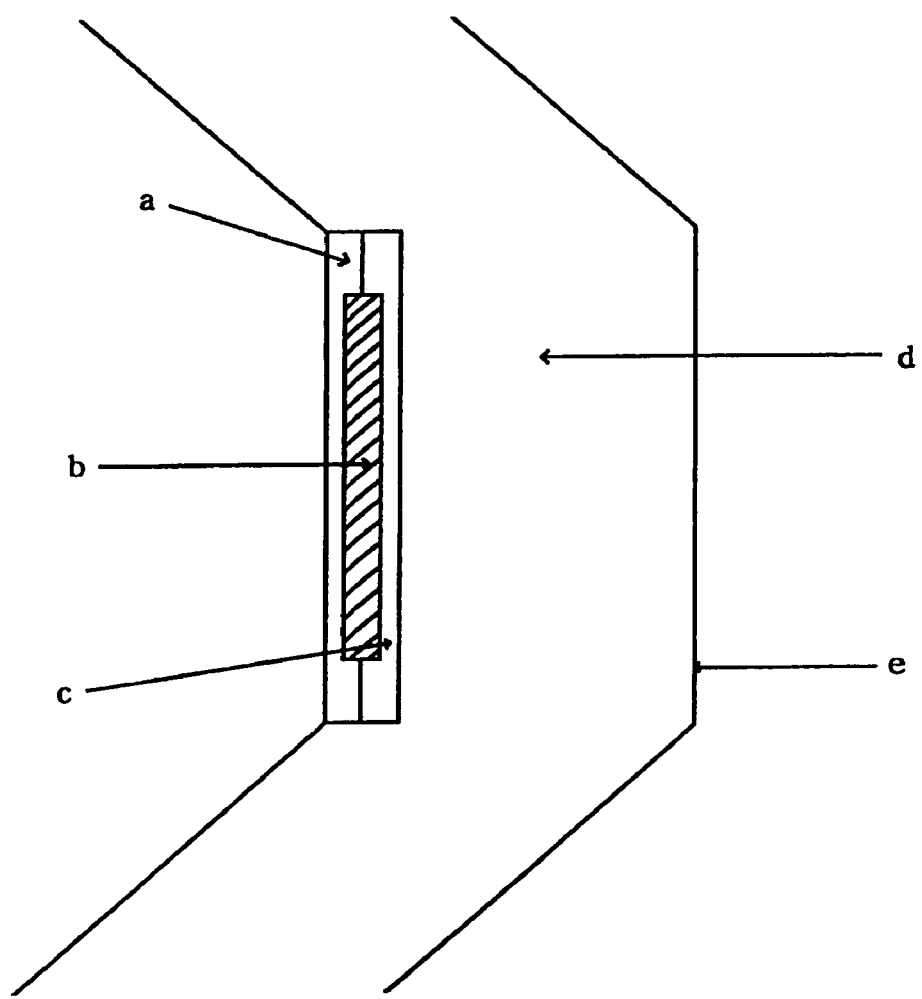
FIG. 1 is a cross sectional view of Examples 14 to 17 as an example for diaper adopting the composition of the present invention. Herein, a and c are polypropylene membrane, b is primary pad in Example 6, d is absorbent matrix and e is vinyl cover.

The present invention is more specifically explained by the following Examples and Experimental Examples, however, is not limited thereto, further it is not intended to limit the scope of the present invention.

Example 1

Infants Diaper Containing Herb Medicine Composition

Example 1.1

Preparation of Composition to be Spread on Diaper 800 g of Sophorae flavescens was washed with distilled water, put into a 5000 ml round flask, mixed with 2000 ml of distilled water, attached to condenser, and extracted by heating for 2 hours. Extracts was filtered with filter cloth and the filtrate was subjected to vacuum concentration to obtain viscous extract 1000 ml.

Example 1.2

Preparation of Composition to be Spread on Diaper 500 g of Sophorae flavescens and 300 g of Phellodendri Cortex were washed with distilled water, and obtained extract 1000 ml according to the method as described in Example 1.1.

Example 1.3

Preparation of Composition to be Spread on Diaper 400 g of Sophorae flavescens, 200 g of Phellodendri Cortex and 200 g of *Dictamnus* alpus were washed with distilled water, and obtained extract 1000 ml according to the method as described in Example 1.1.

Example 1.4

Preparation of Composition to be Spread on Diaper

A) 300 g of Sophorac flavescens, 150 g of Phellodendri Cortex, 100 g of *Artemisia* Folia, 50 g of *Dictamnus* alpus and 100 g of alum were washed with distilled water, put into a 5000 ml round flask, mixed with 2000 ml of distilled water, attached to condenser, and extracted by heating for 2 hours. Extracts was filtered with filter cloth and the filtrate was subjected to vacuum concentration to obtain viscous extract 500 ml.

B) 100 g of alum was pulverized, precipitated in purified water 500 ml at 70–80° C. for 1 hour, filtered and mixed with the viscous extract obtained in A) by a ratio of 1:1 to prepare crude solution.

Example 1.5

Preparation of Composition to be Spread on Diaper 30 kg of Sophorae flavescens, 15 kg of Phellodendri Cortex, 15 kg of *Artemisia* Folia, 10 kg of *Dictamnus* alpus were washed with distilled water, put into a dual tank-container with 1200 L of distilled water, heated to 95–100° C. for 8 hours and so obtained extract was filtered. The filtrate was moved to storage bath of the dual tank, passed through secondary filter, subjected to vacuum concentration at 60° C. to obtain extract of 160 L.

Example 1.6

Preparation of Primary Pad 150 g of natural pulp and 150 ml of the composition prepared in said Example 1.1 were mixed and precipitated for 1 hour without addition of other chemicals to form paper pad of 25 cm×10 cm by using sheet machine. This was dried to prepare 60 primary pads.

Examples 1.7–1.9

Preparation of Primary Pads

Except using the composition prepared in Examples 1.2–1.4, respectively, instead of the composition prepared in said Example 1.1, primary pads were prepared respectively according to the same method with Example 1.6.

Example 1.10

Preparation of Primary Pad

Clean cotton cloth of 25 cm×10 cm was soaked in the composition prepared in said Example 1.1 to allow uniform spread of composition 0.45 g per cotton cloth. This was dried to prepare primary pad.

Examples 1.11–1.13

Preparation of Primary Pads

Except using the composition prepared in Examples 1.2–1.4, respectively, instead of the composition prepared in said Example 1.1, primary pads were prepared respectively according to the same method with Example 1.10.

Example 1.14

Preparation of Sample Pads

The paper primary pad prepared in said example 1.6 was put between the two layers of polypropylene used for preparation of diaper and subjected to heat treatment. This was put on conventional diaper to make shape as shown in FIG. 1.

Examples 1.15–1.17

Preparation of Sample Pads

Except using the paper primary pad prepared in Examples 1.7–1.9 respectively, instead of the paper primary pad prepared in said Example 1.6, according to the same method with Example 1.14, sample pads were prepared, respectively.

Example 1.18

Preparation of Sample Pads

The cotton cloth primary pad prepared in said example 1.10 was put between the two layers of 100% polypropylene used for preparation of diaper and subjected to heat treatment. This was put on conventional diaper to make shape as shown in FIG. 1.

Examples 1.19–1.21

Preparation of Sample Pads

Except using the cotton cloth primary pad prepared in Examples 1.11–1.13, respectively, instead of the cotton cloth primary pad prepared in said Example 1.10, according to the same method with Example 1.18, sample pads were prepared, respectively.

Example 1.22

Preparation of Supplementary Pad for Absorption Stimulation

Discorea Rhizoma was washed, dried and pulverized. 100 g of Discorea Rhizoma powder was added to 36 g of natural pulp, precipitated for 30 minutes without addition of other chemicals to prepare five supplementary pads of 25 cm×10 cm.

Example 1.23

Preparation of Sample Pads

Figure 2:
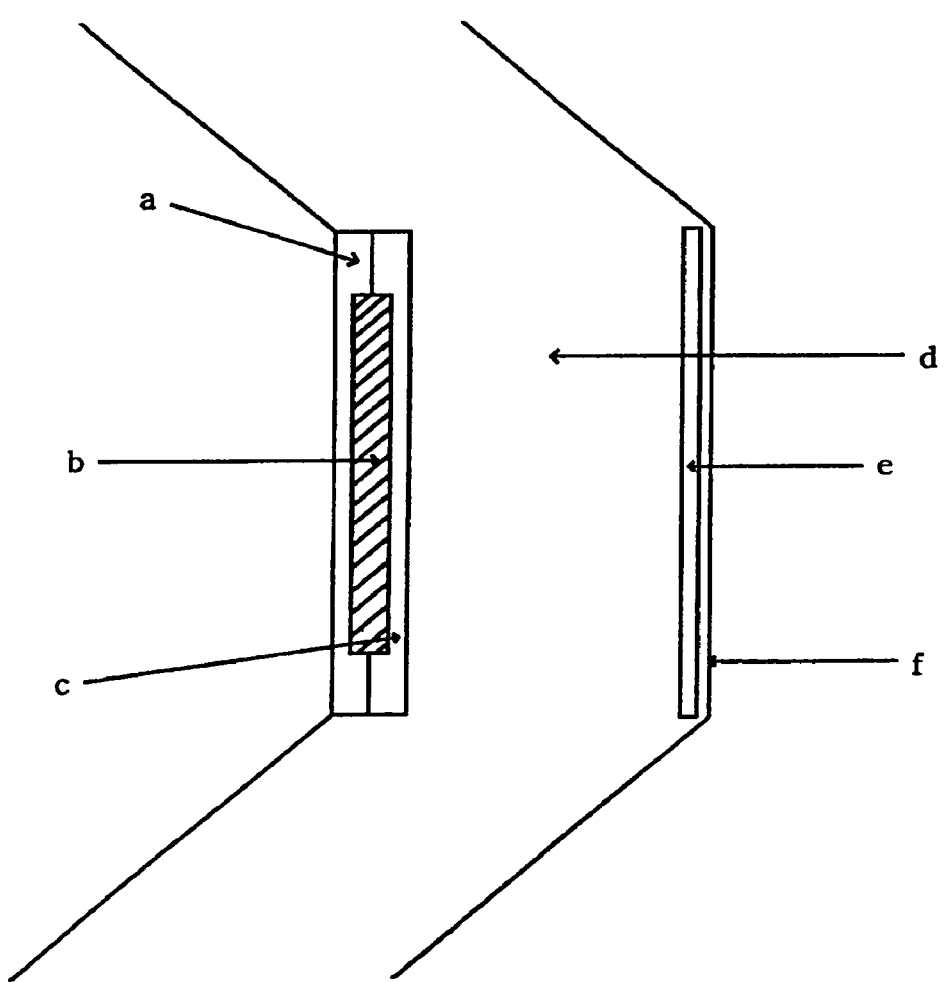
FIG. 2 shows a cross sectional view of Examples 23 to 26 as example for diaper adopting the composition of the present invention. Herein, a and c are polypropylene membrane, b is primary pad in Example 6, d is absorbent matrix and e is supplementary pad containing Discorea Rhizoma powder and f is vinyl cover.

The paper primary pad prepared in said example 1.6 was put between the two layers of 100% polypropylene used for preparation of diaper and subjected to heat treatment. This was put on conventional diaper, and supplementary pad prepared in Example 1.22 was located inside vinyl cover to make shape as shown in FIG. 2.

Examples 1.24–1.26

Preparation of Sample Pads

Except using the paper primary pad prepared in Examples 1.7–1.9 respectively, instead of the paper primary pad prepared in said Example 1.6, according to the same method with Example 1.23, sample pads were prepared, respectively.

Example 1.27

Preparation of Sample Pads

The cotton cloth primary pad prepared in said Example 1.10 was put between the two layers of 100% polypropylene used for preparation of diaper and subjected to heat treatment. This was put on conventional diaper, and supplementary pad prepared in Example 1.22 was located inside vinyl cover to make shape as shown in FIG. 2.

Examples 1.28–1.30

Preparation of Sample Pads

Except using the cotton cloth primary pad prepared in Examples 1.11–1.13, respectively, instead of the cotton cloth primary pad prepared in said Example 1.10, according to the same method with Example 1.27, sample pads were prepared, respectively.

Example 1.31

Preparation of Diaper

The composition prepared in said Example 1.5 was spread on non-woven cloth used for infants diaper (width 12 cm, length 2000 m) to allow uniform spread, i.e. about 1.5 g as dried weight per pad of 45 cm×12 cm. By using the non-woven cloth spread, pulp for pulverization and absorbent structure together, diaper of 45×12 cm was prepared at a diaper factory.

Example 2

Infants Wet Tissue Containing Herb Medicine Composition

Example 2.1

Preparation of Composition for Infants Wet Tissue 800 g of Sophorae flavescens was washed with distilled water, put into a 5000 ml round flask, mixed with 2000 ml of distilled water, attached to condenser, and extracted by heating for 2 hours. Extracts was filtered with filter cloth and the filtrate was subjected to vacuum concentration to obtain viscous extract 1000 ml (dried weight 13.3 g/100 ml). The extract was diluted with purified water to 1:5 ratio to prepare the composition,

Example 2.2

Preparation of Herb Medicine Composition for Infants Wet Tissue 500 g of Sophorae flavescens, 300 g of Phellodendri Cortex were washed with distilled water, and prepared composition according to the method as described in Example 2.1.

Example 2.3

Preparation of Herb Medicine Composition for Infants Wet Tissue 400 g of Sophorae flavescens, 200 g of Phellodendri Cortex and 200 g of *Dictamnus* alpus were washed with distilled water and prepared composition according to the method as described in Example 2.1.

Example 2.4

Preparation of Herb Medicine Composition for Infants Wet Tissue 300 g of Sophorae flavescens, 150 g of Phellodendri Cortex, 50 g of *Dictamnus* alpus and 100 g of alum were washed with distilled water, put into a 5000 ml round flask, mixed with 2000 ml of distilled water, attached to condenser, and extracted by heating for 2 hours. Extracts was filtered with filter cloth and the filtrate was subjected to vacuum concentration to obtain viscous extract 1000 ml (7.5 g/ml based on dried weight). This extract was diluted with distilled water by a ratio of 1:7 to prepare composition.

Example 2.5

Preparation of Herb Medicine Composition for Infants Wet Tissue 30 kg of Sophorae flavescens, 15 kg of Phellodendri Cortex, 10 kg of *Dictamnus* alpus, 15 kg of *Artemisia* Folia were washed with distilled water, put into a dual tank-container with 1200 L of distilled water, heated to 95–100° C. for 8 hours and so obtained extract was passed through primary filter. The filtrate was moved to storage bath of the dual tank, passed through secondary filter, subjected to vacuum concentration at 60° C. to obtain extract of 160 L (5.47 g/ml based on dried weight). The extract was diluted with distilled water by a ratio of 1:7 to prepare composition for infants wet tissue.

Examples 2.6–2.10

Preparation of Infants Wet Tissue

Spun lace non-woven cloth of 15 cm×20 cm was soaked in the composition prepared in said Examples 2.1–2.5, respectively, to allow uniform spread of 0.2 g as dried weight per tissue.

Experimental Example 1

Infants Diaper Containing Herb Medicine Composition

Experimental Example 1.1

Confirmation Experiment I for Toxicity and Negative Effects

The composition prepared in said Example 1.4 was spread five times, each time, 3 ml, every 20 minutes on vaginal orifice and surface of genital organ of four mature male and female rabbits and hourly observation was conducted for genital organ. Furthermore, 6 ml of the composition was spread for continuous 5 days and observation was conducted.

As the result, no deterioration in the surface of genital organ or histological change was observed except contraction of vaginal orifice due to spread of the composition.

Experimental Example 1.2

Confirmation Experiment II for Toxicity and Negative Effects

The primary pads prepared in said Example 1.13 was tested on a 18 month old female infant among the families of the inventors of the present invention by applying the sample pads prepared in Examples 1.17 and 1.21 to conventional cloth and paper diaper, in order, and reaction at the skin contact was observed.

As the result, no change in skin tissue or local side effect due to the use of pad adopting the composition of the present invention was confirmed.

Experimental Example 1.3

Efficacy Experiment on Prevention of Diaper Rash

Using each sample pads prepared in said Examples 1.17 and 1.21, the experiment was performed. Because of the difference in the state of evacuation of individuals, relative comparison of the efficacy with conventional diaper is meaningless, thus infants who had ever experienced rash were selected and reaction after the use of the pad was observed. Test subject was composed of a total of 16 infants, 8 male and 8 female, whose parents agreed to the present efficacy experiment. They were in age of less than 24 months, use diaper all through the day, and experienced 1–14 times of rash in a month. However, there was no particular organic physical disorder except rash.

Guardians were made to continue protection and observation as usual, and the function of the pad was explained so that in case of urination only, the pad could be repeatedly used for 2 or 3 times. Supposing that each infant consumes average 4 pads daily, and a total of 960 pads were divided among 16 guardians, that is, 60 pads enough for 15 days last to each subject, and the result was made to be reported after 15 days.

All 16 infants attended the experiment reported the result after 15 days and the result is as shown in Table. Case when serious rash occurs even one time was determined as "no effect", and the case when rash incidence was decreased to at least 50% compared to the past was determined as "improvement".

TABLE 1

Result of efficacy experiment for Examples 1.17 and 1.21

| Sample pad | Number of subject | Suppression efficacy for diaper rash | | | Total application time (h) |
|---|---|---|---|---|---|
| | | No effect | Improved | No rash | |
| Ex. 1.17 | 1 (female) | — | — | 1 | 360 |
| Ex. 1.21 | 8 (male) | — | 1 | 7 | 2880 |
| | 7 (female) | — | — | 7 | 2520 |
| Total | 16 | — | 1 | 15 | 5760 |

As can be seen from the above table, among 15 infants wearing the sample pad of Example 1.21, a 16 month-old male infant with rash history of average 4 times in a month experienced slight rash one time, and the rest 14 subject (93.3%) did not experience rash. Further, a female infant with rash history of average 14 times in a month was liable to serious rash due to bad diarrhea, but rash did not occur by the use of the sample pad according to the present invention, thereby confirming preventive effect against rash. In addition, even when the pad was dried and used again after receiving urine 2–3 times, skin of subject remained dry due to remaining drug substance. Further, no negative effect due to application of sample pad of the present invention was observed.

Experimental Example 1.4

Efficacy Experiment for Prevention of Diaper Rash

Efficacy experiment was conducted for each sample pad prepared in Examples 1.18 and 1.19 by the same method as in Experimental Example 1.3. The result is as shown in Tables 2 and 3.

TABLE 2

Test Result for Example 1.18

| Sample pad | Number of subject | Efficacy against diaper rash | | | Total application time (h) |
|---|---|---|---|---|---|
| | | No effect | Improved | No rash | |
| Ex. 1.18 | 8 (male) | — | 3 | 5 | 2880 |
| | 10 (female) | — | 4 | 6 | 3600 |
| Total | 18 | — | 7 | 11 | 6840 |

TABLE 3

Test Result for Example 1.19

| Sample pad | Number of subject | Efficacy against diaper rash | | | Total application time (h) |
|---|---|---|---|---|---|
| | | No effect | Improved | No rash | |
| Ex. 1.19 | 9 (male) | — | 3 | 6 | 3240 |
| | 10 (female) | — | 2 | 8 | 3600 |
| Total | 19 | — | 5 | 14 | 6840 |

As shown in above Table, rash did not occur in 11 infants (61.1%) among 18 subject wearing sample pad of Example 1.18, and the rest 7 infants (38.9%) showed improvement. Further, even in the result for Example 1.19, rash did not occur in 14 of 19 subject (73.7%), and 5 subject (26.3%) showed improvement. Considering that a part of the infants attended the experiment for Examples 1.18 and 1.19 were suffering from rash, it was confirmed that wearing of the pad of the present invention exhibited preventive effect against rash. Additionally, no skin negative effect was reported due to wearing of the pad of the present invention, but in case of infants wearing the pad of the present invention, which was attached on conventional cloth diaper, it was reported that the cloth diaper was smeared with drug substance.

Experimental Example 1.5

Experiment for Local Cooling Effect

The inventors of the present invention intentionally cause rash at left forearm. The primary pad prepared in Example 1.21 was moistened with 5 ml of water and attached to rash region. Before the attachment, and 30 minutes and 1 hour after the attachment, skin temperature was measured by infrared body heat examination, and the temperature was compared.

The result is as given in Table 4. It was confirmed that temperature declined from 25.77° C. before wearing the pad to 23.72° C., 30 minutes after the attachment of pad and 23.78° C., 1 hour after the attachment, that is, about 2° C. decline was confirmed.

TABLE 4

| Temperature Measurement Time | Temp. (° C.) | Difference from the Temperature before the attachment (° C.) |
| --- | --- | --- |
| Before attachment | 25.77 | — |
| 30 min. after attachment | 23.72 | −2.05 |
| 1 hr. after attachment | 23.78 | −1.99 |

The primary pad prepared in Example 1.21 was moistened with 10 ml of urine and attached to left knee joint. Temperature was measured before, 30 minutes after attachment and 30 minutes after removal.

The result is given in Table 5. It was confirmed that normal temperature before the attachment was 24.62° C., decreased to 22.65° C. after attachment, i.e. 1.97° C. decrease, and 0.76° C. was again increased 30 minutes after complete removal.

TABLE 5

| Temperature Measurement Time | Temp. (° C.) | Difference from the Temperature before the attachment (° C.) |
| --- | --- | --- |
| Before attachment | 24.62 | — |
| 30 min. after attachment | 22.65 | −1.97 |
| 30 min. after attachment | 23.41 | +0.76 |

The experimental result given above demonstrates that the composition of the present invention spread on primary pad causes skin cooling and blood vessel contraction when evaporating with moisture from urine. Assuming that significant body heat change is about 0.5° C., the local cooling effect of the pad is inferred as important mechanism for rash treatment.

Experimental Example 1.6

Absorbency Experiment for Supplementary Pad

To confirm absorption stimulation effect of the supplementary pad, comparative experiment was conducted as follows.

Supplementary pad for absorption experiment was prepared. Discorea Rhizoma was washed, dried and pulverized. To 36 g of natural pulp, losin size (alkyl ketone dimmer 20%) to protect water infiltration was added to 0.43% based on weight of natural pulp, Discorea Rhizoma 100 g was added and precipitated for 30 minutes without addition of other chemicals to prepare 5 supplementary pads of 25 cm×10 cm for absorbency test.

Further, as control, supplementary pad was prepared by excluding Diacorea Rhizoma. That is, 0.43% (based on weight of natural pulp) of losin size was added to 36 g of natural pulp, mixed and precipitated for 30 minutes without addition of other chemicals to prepare 5 control supplementary pads of 25 cm×10 cm.

50 ml of 2% Rhodan ammonium solution was added, and supplementary pads for absorption test and control prepared as above were cut into pieces of 2.5 cm×2.5 cm. This was folded into paper ship and floated on 50 ml of 2% Rhodan ammonium solution filled in 12 cm-diameter petri dish. 0.1 ml of 1% ferrous chloride solution was dropped and determined the time point when 3 or more red spots appeared. The experimental method described above is known in paper manufacturing industry as absorbency test method.

As the result, despite that the supplementary pad containing Discorea Rhizoma powder included losin size to protect water infiltration, 3 or more red spots appeared within 3 seconds, confirming rapid absorption of Rhodan solution, in contrast, supplementary pad without Discorea Rhizoma powder (control) needed 45 seconds, revealing superior absorbency of supplementary pad containing Discorea Rhizoma powder.

Experimental Example 1.7

General Consumer Test for Diaper Rash Prevention Effect 50 infants among infants living in Seoul, Chungju and Daeku, Korea were randomly selected, let to wear diaper adopting the composition of the present and the efficacy was tested. As the diaper adopting the composition of the present invention, infant diaper of Example 1.18 adopting the composition of Example 5 was used.

Excepting 10% infants without rash experience, most of 90% subject admitted the rash prevention effect as superior (60% of the subject) or significant (25% of the subject). Further, as result of wearing diaper adopting the composition of the present invention, it was confirmed that dampness hardly occurred at the skin contact and skin was kept dry compared to conventional diaper, and no subject reported occurrence of negative effect at the skin contact.

Experimental Example 2

Infants Wet Tissue Containing Herb Medicine Composition

Experimental Example 2.1

Confirmation Experiment for Toxicity and Negative Effect

The composition prepared in said Example 2.4 was spread five times, each time, 3 ml, every 20 minutes on vaginal orifice and surface of genital organ of four mature male and female rabbits and hourly observation was conducted for 6 hours. Further, 6 ml of the composition was spread for continuous 5 days and observation was conducted. As the result, neither deterioration in the surface of genital organ nor histological change was observed except contraction of vaginal orifice due to spread of the composition.

Experimental Example 2.2

Confirmation Experiment for Toxicity and Negative Effect

Tissue prepared in Application examples 2.1–2.5 was applied to 4 male and female infants younger than 24 months including families of the inventors of the present invention and reaction at skin contact was observed. As the result, no change in skin tissue or local side effect due to the use of the tissue adopting the composition of the present invention was observed.

Experimental Example 2.3

Efficacy Experiment for Infant Wet Tissue

Spun lace non-woven cloth tissue prepared in Examples 2.6 and 2.10 were tested with infants for efficacy.

5 male and 7 female infants younger than 24 months who currently wear diaper were selected, and a total of 60 tissues, that is, 30 wet tissues prepared in Example 2.6 and 30 tissues prepared in Example 2.10, was given to each guardian and let them report the result after the use.

As result of efficacy experiment, it was confirmed that wet tissue of the present invention exhibits cleaning function, causes no slippery tackiness, allows skin to be dry contrary to conventional wet tissue, thereby suppressing the use of powder spread and ointments.

Sanitary materials, particularly diaper and wet tissue, adopting the herb medicine composition of the present invention which was prepared by using herb medicine with special efficacy among harmless natural drug substances, as described above, provides effect of preventing and even treating diaper rash besides the original utility, thus can suppress abuse of adrenocortical hormone ointment or non-steroidal ointment and can basically protect infants from skin diseases related to diaper rash.

What is claimed is:

1. A diaper comprising:
    a primary pad made of a mixture of an herb medicine composition containing Sophorae flavescens and natural pulp; and
    a supplementary pad for absorption stimulation containing Discorea rhizoma.

2. The diaper in claim 1, wherein the herb medicine composition further comprises Phellodendri cortex, *Artemisia* folia, *Dictamnus* alpus and Alum, and the composition is consisted of 20–85% of Sophorae flavescens, 2–50% of Phellodendri cortex, 2–30% of *Artemisia* folia, 1–35% of *Dictamnus* alpus, and 10–40% of Alum, based on total dried weight.

3. The diaper in claim 2, wherein the composition is in a form selected from a group consisting of powder, extract and infusion.

* * * * *